US009563978B2

(12) United States Patent
Masumoto (10) Patent No.: US 9,563,978 B2
(45) Date of Patent: Feb. 7, 2017

(54) IMAGE GENERATION APPARATUS, METHOD, AND MEDIUM WITH IMAGE GENERATION PROGRAM RECORDED THEREON

(71) Applicant: FUJIFILM Corporation, Tokyo (JP)

(72) Inventor: Jun Masumoto, Tokyo (JP)

(73) Assignee: FUJIFILM CORPORATION, Tokyo (JP)

( * ) Notice: Subject to any disclaimer, the term of this patent is extended or adjusted under 35 U.S.C. 154(b) by 135 days.

(21) Appl. No.: 14/483,376

(22) Filed: Sep. 11, 2014

(65) Prior Publication Data

US 2014/0375631 A1    Dec. 25, 2014

Related U.S. Application Data

(63) Continuation of application No. PCT/JP2013/001634, filed on Mar. 13, 2013.

(30) Foreign Application Priority Data

Mar. 14, 2012    (JP) .................................. 2012-056977

(51) Int. Cl.
    *G06T 15/00*    (2011.01)
    *G06T 15/08*    (2011.01)
    (Continued)

(52) U.S. Cl.
    CPC ............... *G06T 15/08* (2013.01); *A61B 6/466* (2013.01); *A61B 6/504* (2013.01); *A61B 8/0891* (2013.01);
    (Continued)

(58) Field of Classification Search
    None
    See application file for complete search history.

(56) References Cited

U.S. PATENT DOCUMENTS

2004/0249270 A1    12/2004    Kondo et al.
2008/0278488 A1    11/2008    Rabben et al.
2011/0242097 A1    10/2011    Miyamoto

FOREIGN PATENT DOCUMENTS

CN    102208118 A    10/2011
EP    2 372 661 A2    10/2011
(Continued)

OTHER PUBLICATIONS

International Search Report (ISR) (PCT Form PCT/ISA/210), in PCT/JP2013/001634, dated Jun. 4, 2013.
(Continued)

*Primary Examiner* — Peter Hoang
(74) *Attorney, Agent, or Firm* — McGinn IP Law Group, PLLC.

(57) ABSTRACT

When generating a pseudo three-dimensional image by performing volume rendering on a three-dimensional image using an opacity curve that defines the relationship between pixel value and opacity, identifying a whole region representing a predetermined target object from the three-dimensional image, setting a base opacity curve to the identified whole region, obtaining, with respect to each of at least some pixels in the identified whole region, a representative value in an adjacent region of a pixel concerned, and setting an opacity curve obtained by modifying the base opacity curve using the obtained representative value as the opacity curve to be applied to the pixel concerned in the volume rendering.

12 Claims, 5 Drawing Sheets

(51) Int. Cl.
*A61B 6/00* (2006.01)
*A61B 8/08* (2006.01)
*A61B 8/00* (2006.01)
*A61B 5/00* (2006.01)

(52) U.S. Cl.
CPC ................ *A61B 8/466* (2013.01); *A61B 5/489* (2013.01); *A61B 8/483* (2013.01); *A61B 2576/00* (2013.01); *G06T 2200/04* (2013.01); *G06T 2210/41* (2013.01)

(56) References Cited

FOREIGN PATENT DOCUMENTS

| | | |
|---|---|---|
| JP | 2004-283373 A | 10/2004 |
| JP | 2008-086658 A | 4/2008 |
| JP | 2011-212219 A | 10/2011 |

OTHER PUBLICATIONS

H. Imai, "I see!! The Bible of the Way of Thinking and Processing—Three-Dimensional Medical Image", Shujunsha, P. 105, 2003 and an English translation thereof.
Extended European Search Report dated Oct. 22, 2015.
Japanese Office Action dated Jun. 2, 2015 with an English translation thereof.
Chinese Office Action dated May 3, 2016 with an English translation thereof.

IMAGE GENERATION APPARATUS, METHOD, AND MEDIUM WITH IMAGE GENERATION PROGRAM RECORDED THEREON

CROSS-REFERENCE TO RELATED APPLICATIONS

This application is a Continuation of PCT International Application No. PCT/JP2013/001634 filed on Mar. 13, 2013, which claims priority under 35 U.S.C. §119 (a) to Japanese Patent Application No. 2012-056977 filed on Mar. 14, 2012. Each of the above applications is hereby expressly incorporated by reference, in its entirety, into the present application.

BACKGROUND OF THE INVENTION

Technical Field

The present invention relates to an image generation apparatus, method, and program that generates a pseudo three-dimensional image by performing volume rendering on a three-dimensional image.

Background Art

Heretofore, processing for generating and displaying a pseudo three-dimensional image has been performed in which three-dimensional image data of a subject obtained by CT equipment, MRI equipment, ultrasonic diagnostic equipment, or the like are stereoscopically visualized on a two-dimensional plane using computer graphics technologies in order to facilitate understanding of a three-dimensional structure of the subject and the like. As a method for generating such a pseudo three-dimensional image, a volume rendering method is known in which opacity and color information of R, G, B are set to each pixel value (voxel value) constituting a three-dimensional image and the visualization is achieved by performing ray-casting on each pixel on a projection plane from the observation side.

For the opacity or color information set (referred to as opacity curve and color map respectively) which is set to each pixel value, it is common to give one set to one three-dimensional image. But this causes a problem that different tissues having the same signal value cannot be displayed distinguishably. In response to this, when generating one image representing a plurality of objects (e.g., bone, blood vessel, heart, liver, and the like) by volume render, a literature, H. Imai, "I see! ! The Bible of the Way of Thinking and Processing—Three-Dimensional Medical Image", Shujunsha, P. 105, 2003, proposes that different tissues having the same signal value are represented by different color or opacity by applying a different color map and/or opacity curve to each object region.

DISCLOSURE OF THE INVENTION

In the meantime, in CT imaging of a blood vessel, for example, a method that further visualizes and makes that portion extractable by performing imaging after injecting a special liquid called a contrast agent is sometimes used so that pixel values of the blood vessel differ from those of other organs in a three-dimensional image. In this case, however, a variation in pixel value occurs from place to place even in the same blood vessel region due to the imaging timing or the amount of the contrast agent. Therefore, when generating an image that represents a wide range of blood vessel region, even for one target object tissue of blood vessel, the simple application of one color map and/or an opacity curve causes a problem that a three-dimensional morphology of the entire blood vessel cannot be represented accurately.

Figure 6:
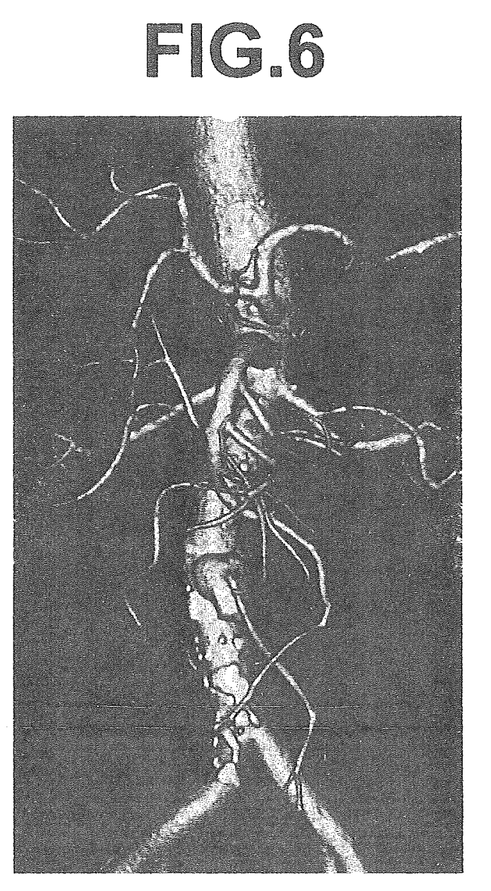
FIG. 6 is a drawing illustrating an example image generated by conventional technology.
Figure 7:
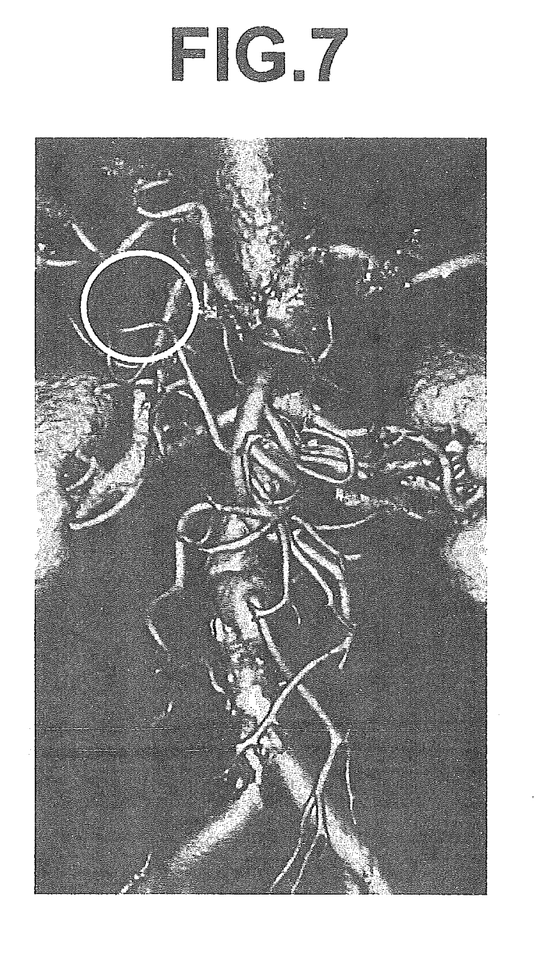
FIG. 7 is a drawing illustrating an example image generated by conventional technology.

The problem due to the variation in pixel value may possibly occur by a partial volume effect. In particular, for thin blood vessels of a diameter represented by several pixels, there may be a case where a blood vessel which should have actually a high pixel value is imaged with a pixel value lower than the real value influenced by the surrounding pixel values at the time of the imaging. This may result in that, in an image generated by applying one color map and opacity curve which is based on the pixel value distribution of a thick blood vessel, a thick blood vessel portion appears clearly but a thin blood vessel portion is not visualized, as shown, for example, in FIG. 6, while, in an image generated by one color map and opacity curve, which are the aforementioned color map and opacity curve translated according to the pixel value distribution of a thin blood vessel, a thin blood vessel portion is visible (refer to the portion enclosed by the white circle) but a thick blood vessel portion appears over inflated, as shown in FIG. 7.

Japanese Unexamined Patent Publication No 2011-212219 proposes a method for dynamically correcting color map and/or opacity curve with respect to each image, but the method is based on the assumption that the depiction range of each image is so small that the variation in pixel value is negligible and related to how to decide one opacity curve used for generating on image. Therefore, the method does not solve the aforementioned problem when generating an image representing a wider object range.

In view of the circumstances described above, it is an object of the present invention to provide an image generation apparatus, method, and program capable of generating an image which depicts three-dimensional morphology of a predetermined target object more accurately when generating a pseudo three-dimensional image by performing volume rendering.

An image generation apparatus of the present invention includes an image generation section that generates a pseudo three-dimensional image by performing volume rendering on a three-dimensional image using an opacity curve that defines the relationship between pixel value and opacity, a region identification section that identifies a whole region representing a predetermined target object from the three-dimensional image, and an opacity curve setting section that sets a base opacity curve to the identified whole region, obtains, with respect to each of at least some pixels in the identified whole region, a representative value of pixel values in an adjacent region of a pixel concerned, and sets an opacity curve obtained by modifying the base opacity curve using the obtained representative value as the opacity curve to be applied to the pixel concerned in the volume rendering (first image generation apparatus).

The opacity curve setting section may be a section that obtains, with respect to each of the at least some pixels, a shift amount of opacity curve based on a subtraction value obtained by subtracting a representative value of pixel values in the whole region from the representative value of pixels in the adjacent region of the pixel concerned and sets an opacity curve obtained by shifting the base opacity curve by the obtained shift amount in a pixel value direction as the opacity curve to be set to the pixel concerned in the volume rendering.

The term "pixel value direction" as used herein refers to, when the opacity curve is set in a coordinate system with one axis (e.g., horizontal axis) representing the pixel value and the other axis (e.g., vertical axis) representing the opacity, a direction of the axis representing the pixel value.

When obtaining the shift amount based on the subtraction value, a value having the same positive or negative sign as that of the subtraction value is obtained as the shift amount. Here, the absolute value of the shift amount may be the same as the absolute value of the subtraction value or a value obtained by multiplying the value with a predetermined coefficient other than 1. Thus, "shifting by the shift amount" refers to shifting to plus direction of the axis representing the pixel value if the sign of the shift amount is plus while shifting to minus direction of the axis representing the pixel value if the sign of the shift amount is minus.

In the image generation apparatus of the present invention, the opacity curve setting section may be a section that obtains, with respect to each of some pixels obtained by sampling the pixels in the whole region at a predetermined interval, a representative value of pixels in an adjacent region of a pixel concerned, obtains a shift amount of opacity curve based on a difference between the obtained representative value and a representative value of pixel values in the whole region, and sets an opacity curve obtained by shifting the base opacity curve by the obtained shift amount to a pixel value direction as the opacity curve to be applied to the pixel concerned, and obtains, with respect to each of pixels in the whole region other than the sampled some pixels, an estimated value of shift amount at a pixel concerned by interpolation using the shift amount of each of the two or more sampled pixels located adjacent to the pixel concerned and sets an opacity curve obtained by shifting the base opacity curve by the determined estimated value in a pixel value direction as the opacity curve to be applied to the pixel concerned in the volume rendering.

The representative value of the pixel values in the adjacent region may be a mode value, a median value, or an average value of the pixel values in the adjacent region, an average value of pixel values of all pixel values in the adjacent region which fall in a range of predetermined width of pixel values from the mode value or the median value of the pixels in the adjacent region, or a mode value or a median value of pixel values of all pixel values in the adjacent region which fall in a range of predetermined width of pixel values from the mode value or the median value of the pixels in the adjacent region.

At this time, the representative value of the pixels in the whole region may be a value of the same type as that of the representative value of the pixels in the adjacent region or a value of different type from that of the representative value of the pixels in the adjacent region. For example, if the representative value of the pixels in the adjacent region is the average value, the representative value of the pixels in the whole region may be the average value or the mode value of the pixels in the whole region.

In the image generation apparatus of the present invention described above, the image generation section may be a section that generates a pseudo three-dimensional image by performing volume rendering on the three-dimensional image using a color map that defines the relationship between pixel value and display color, and the apparatus may further includes a color map setting section that sets a base color map to the identified whole region and calculates, with respect to each of at least some pixels in the identified whole region, a representative value of pixel values in an adjacent region of a pixel concerned, and sets a color map obtained by modifying the set base color map using the calculated representative value as the color map to be applied to the pixel concerned in the volume rendering.

An image generation apparatus of the present invention includes an image generation section that generates a pseudo three-dimensional image by performing volume rendering on a three-dimensional image using a color map that defines the relationship between pixel value and display color, a region identification section that identifies a whole region representing a predetermined target object from the three-dimensional image, and a color map setting section that sets a base color map to the identified whole region, calculates, with respect to each of at least some pixels in the identified whole region, a representative value of pixel values in an adjacent region of a pixel concerned, and sets a color map obtained by modifying the set base color map using the calculated representative value as the color map to be applied to the pixel concerned in the volume rendering (second image generation apparatus).

In the first and the second image generation apparatuses, the predetermined target object may be a blood vessel.

First and second image generation methods of the present invention are methods, each performs the processing performed by each section of the first or the second image generation apparatus with at least one computer.

First and second image generation programs of the present invention are programs, each causes at least one computer to perform the processing performed by each section of the first or the second image generation apparatus. The programs are recorded on recording media, such as CD-ROM, DVD, and the like, or recorded on an auxiliary storage of a server computer or a network storage in a downloadable manner and supplied to the user.

According to the first image generation apparatus, method, and program of the present invention, when generating a pseudo three-dimensional image by performing volume rendering on a three-dimensional image using an opacity curve that defines the relationship between pixel value and opacity, a whole region representing a predetermined target object is identified from the three-dimensional image, a base opacity curve is set to the identified whole region, with respect to each of at least some pixels in the identified whole region, a representative value of pixel values in an adjacent region of a pixel concerned is obtained, and an opacity curve obtained by modifying the base opacity curve using the obtained representative value is set as the opacity curve to be applied to the pixel concerned in the volume rendering. This allows an opacity curve appropriate for depicting the pixel be applied to each of all pixels in the region representing the predetermined target object, whereby an image more accurately depicting three-dimensional morphology of the predetermined target object may be generated. This effect is more significant if the predetermined target object is a blood vessel and further significant if the three-dimensional image is an image obtained by injecting a contrast agent into the blood vessel.

In the image generation apparatus, method, and program of the present invention described above, if an arrangement is adopted in which, with respect to each of some pixels obtained by sampling the pixels in the whole region at a predetermined interval, a representative value of pixels in an adjacent region of a pixel concerned is obtained, a shift amount of opacity curve based on a difference between the obtained representative value and a representative value of pixel values in the whole region is obtained, and an opacity curve obtained by shifting the base opacity curve by the obtained shift amount to a pixel value direction is set as the opacity curve to be applied to the pixel concerned, and, with respect to each of pixels in the whole region other than the sampled some pixels, an estimated value of shift amount at a pixel concerned is obtained by interpolation using the shift amount of each of the two or more sampled pixels located adjacent to the pixel concerned, and an opacity curve obtained by shifting the base opacity curve by the determined estimated value in a pixel value direction is set as the opacity curve to be applied to the pixel concerned in the volume rendering, the arithmetic operation may be speeded up.

Further, if the representative value of the pixel values in the adjacent region is the mode value or the median value of the pixel values in the adjacent region, an extreme value due to noise, if present in the adjacent region, is less likely to be reflected to the representative value.

Further, if the representative value of the pixel values in the adjacent region is an average value, a mode value, or a median value of pixel values of all pixel values in the adjacent region which fall in a range of predetermined width of pixel values from the mode value or the median value of the pixels in the adjacent region, an extreme value that presents on the maximum or the minimum side of the pixel values in the adjacent region is less likely to be reflected to the representative value.

Still further, in the image generation apparatus, method, and program of the present invention described above, if an arrangement is adopted in which a base color map is set to the identified whole region and, with respect to each of at least some pixels in the identified whole region, a representative value of pixel values in an adjacent region of a pixel concerned is calculated, and a color map obtained by modifying the set base color map using the calculated representative value is set as the color map to be applied to the pixel concerned in the volume rendering, a color map appropriate for depicting the pixel may be applied to each of all pixels in the region representing the predetermined target object, whereby an image more accurately depicting three-dimensional morphology of the predetermined target object may be generated.

According to the second image generation apparatus, method, and program of the present invention, when generating a pseudo three-dimensional image by performing volume rendering on a three-dimensional image using a color map that defines the relationship between pixel value and display color, a whole region representing a predetermined target object is identified from the three-dimensional image, a base color map is set to the identified whole region, with respect to each of at least some pixels in the identified whole region, a representative value of pixel values in an adjacent region of a pixel concerned is calculated, and a color map obtained by modifying the set base color map using the calculated representative value is set as the color map to be applied to the pixel concerned in the volume rendering. This allows a color map appropriate for depicting the pixel to be applied to each of all pixels in the region representing the predetermined target object, whereby an image more accurately depicting three-dimensional morphology of the predetermined target object may be generated.

BEST MODE FOR CARRYING OUT THE INVENTION

Figure 1:
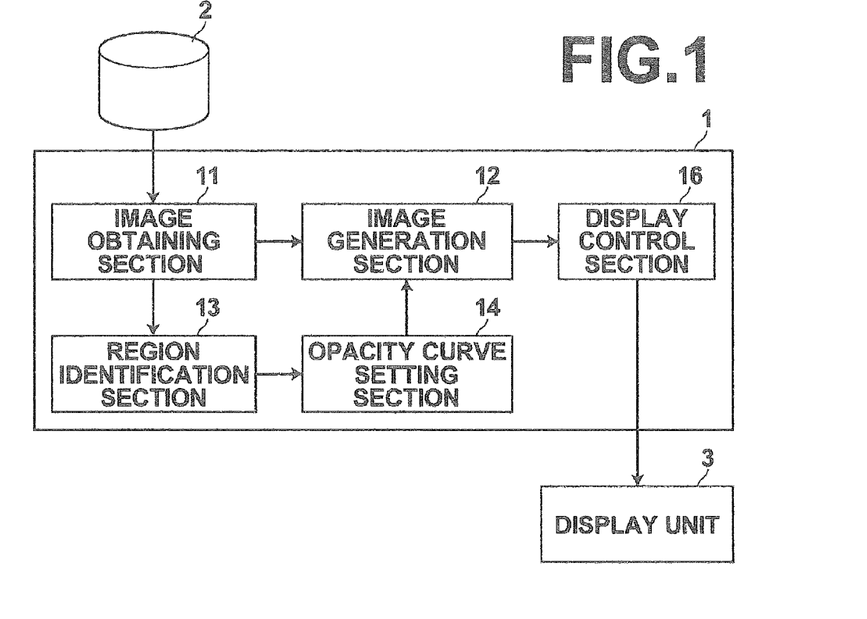
FIG. 1 is a schematic block diagram of an image generation apparatus of a first embodiment.

Hereinafter, a first embodiment of the present invention will be described with reference to the accompanying drawings. FIG. 1 is a block diagram of an image generation apparatus 1, illustrating a schematic configuration thereof. The configuration of the image generation apparatus 1 illustrated in FIG. 1 is realized by executing an image generation program read into an auxiliary storage unit on a computer. Here, the image generation program is recorded on a recording medium, such as CD-ROM or the like, or distributed via a network, such as the Internet or the like, and installed on the computer. The image generation program defines image obtaining processing, image generation processing, region specification processing, opacity curve setting processing, and display control processing, as the processing to be performed by CPU of the computer. When each processing described above is executed by the CPU according to the definition described above, the computer functions as an image obtaining section 11, an image generation section 12, a region identification section 13, an opacity curve setting section 14, and a display control section 16, which will be described later.

The image generation apparatus 1 is connected to a storage unit 2, such as a hard disk drive or the like, and a display unit 3, such as a display or the like. The storage unit 2 stores three-dimensional image data (three-dimensional images) obtained by imaging predetermined target objects with imaging equipment, such as CT, MRI, PET, SPECT, ultrasonic imaging equipment, and the like. A three-dimensional image is a collection of pixel data in a three-dimensional space and may be obtained by stacking a plurality of tomographic images obtained by imaging equipment. The image obtaining section 11 obtains the three-dimensional image stored in the storage unit 2 and stores the image in a storage device built in the image generation apparatus 1 or a storage unit connected to the image generation apparatus, such as a hard disk drive.

The region identification section 13 identifies a whole region representing a predetermined target object from the three-dimensional image obtained by the image obtaining section 11. Here, a whole region representing a predetermined target object refers to a region that includes all regions representing the predetermined target object and does not include other regions. Hereinafter, a description will be made of a case in which the predetermined target object is a blood vessel. The region identification section 13 extracts a region representing the blood vessel (blood vessel region) from the three-dimensional image and identifies the extracted region as a whole region. Here, the extraction of the blood vessel region may be obtained by threshold method, Region Growing method, Level Set method, and other various types of image processing.

For example, the region identification section 13 searches a linear structure with respect of each local region in the three dimensional image by calculating eigenvalues of a 3×3

Hessian matrix. In a region where a linear structure is included, one of the three eigenvalues is close to 0 and the other two are relatively large. The eigenvector corresponding to the eigenvalue close to 0 indicates the principal axis direction of the linear structure. The region identification section 13 makes use of this relationship and determines the likelihood of linear structure with respect to each local region based on eigenvalues of the Hessian matrix. For a local region where a linear structure is identified, the center point thereof is detected as a candidate point. Then, the candidate points detected by the search are connected based on a given algorithm. This builds a tree structure formed of the candidate points and blood vessel branches (edges) connecting the candidate points. The coordinate information of the plurality of detected candidate points and vector information indicating the directions of the blood vessel branches are stored in a memory with the identifiers of the candidate points and blood vessel branches. Then, a blood vessel contour (blood vessel external wall) is identified on a cross-section perpendicular to the blood vessel route with respect to each detected candidate point based on the surrounding pixel values. The shape may be identified by known segmentation methods as represented by the Graph-Cuts. The blood vessel region which is a tubular structure is extracted, and information necessary to identify the extracted blood vessel region is generated and stored in a memory through the aforementioned processing.

The opacity curve setting section 14 sets an opacity curve to be applied, in volume rendering, to each pixel in the blood vessel region identified by the region identification section 13. The opacity curve defines the relationship between pixel value and opacity and may be represented by a function of pixel value. More specifically, a base opacity curve is set to the blood vessel region first. For example, a pixel value distribution of the blood vessel region and a pixel value distribution of the neighboring region are checked with the three-dimensional image, and pixel values serving as the boundary separating the blood vessel region from other regions are obtained based on these distributions. Then, an opacity curve in which opacity "0" changes to a value other than "0" or opacity "1" changes to a value other than "1" is set adjacent to the pixel values. The opacity curve may be a curve in which the opacity changes in stepwise from "0" to "1" or a curve in which the opacity changes at a predetermined slope according to increase or decrease in the pixel value.

Then, the opacity curve setting section 14 obtains, with respect to each of some pixels obtained by three-dimensionally sampling the pixels in the blood vessel region at a predetermined interval, a subtraction value obtained by subtracting the average value of the pixel values in the blood vessel region from the average value of the pixel values of an adjacent region (e.g., region in the range of 1 cm in up, down, left, right, front, and back directions) of a pixel concerned as a shift amount of the opacity curve, and sets an opacity curve obtained by shifting the base opacity curve by the determined shift amount in a pixel value direction as the opacity curve to be applied to the pixel concerned. That is, the opacity curve setting section 14 sets an opacity curve represented, when the pixel value is taken as a variable v, the base opacity curve is taken as OD (v), and the determined shift amount is taken as m, by $O(v)=OD(v-m)$ to each of the sampled pixels.

Further, the opacity curve setting section 14 obtains, with respect to each of pixels in the blood vessel region other than the sampled some pixels, an estimated value of shift amount at a pixel concerned by interpolation using the shift amount of each of the two or more sampled pixels located adjacent to the pixel concerned, and sets an opacity curve obtained by shifting the base opacity curve by the determined estimated value in a pixel value direction as the opacity curve to be applied to the pixel concerned.

The image generation section 12 generates a pseudo three-dimensional image by performing volume rendering on the three-dimensional image using the opacity curve set by the opacity curve setting section 14. The display control section 16 displays the pseudo three-dimensional image generated by the image generation section 12 on the display unit 3.

Figure 2:
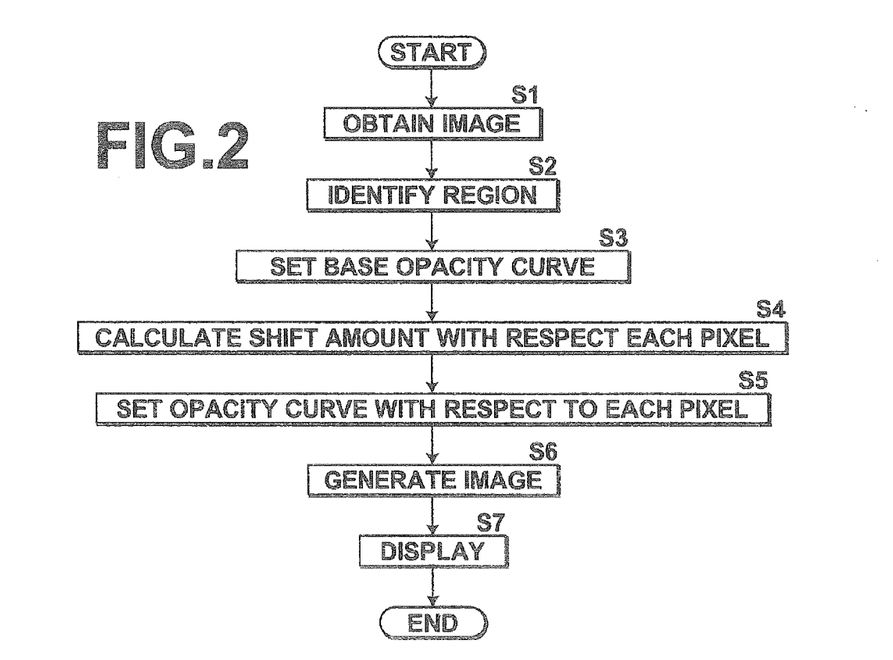
FIG. 2 is a flowchart illustrating an operation of the image generation apparatus of the first embodiment.

FIG. 2 is a flowchart illustrating an operation of the image generation apparatus 1. As illustrated, first, the image obtaining section 11 obtains a three-dimensional image stored in the storage unit 2 (S1). Then, the region identification section 13 extracts a region representing a blood vessel from the three-dimensional image obtained by the image obtaining section 11 and identifies the extracted region as a whole region (S2). Then, the opacity curve setting section 14 sets a base opacity curve to the blood vessel region (S3). Further, the opacity curve setting section 14 obtains, with respect to each of some pixels obtained by three-dimensionally sampling the pixels in the blood vessel region at a predetermined interval, a subtraction value obtained by subtracting the average value of the pixel values in the blood vessel region from the average value of the pixel values of the adjacent region of a pixel concerned as a shift amount of the opacity curve and obtains, with respect to each of pixels in the blood vessel region other than the sampled some pixels, an estimated value of the shift amount at a pixel concerned by interpolation using the shift amount of each of the two or more sampled pixels located adjacent to the pixel concerned (S4).

Further, the opacity curve setting section 14 sets, with respect to each of the sampled some pixels, an opacity curve obtained by shifting the base opacity curve by the shift amount determined in step S4 in a pixel value direction as the opacity curve to be applied to the pixel concerned and sets, with respect to each of pixels other than the sampled some pixels, an opacity curve obtained by shifting the base opacity curve by the estimated value determined in step S4 in a pixel value direction as the opacity curve to be applied to the pixel concerned (S5).

Thereafter, the image generation section 12 generate a pseudo three-dimensional image by performing volume rendering on the three-dimensional image using the opacity curve set by the opacity curve setting section 14 (S6). Then, the display control section 16 displays the pseudo three-dimensional image generated by the image generation section 12 on the display unit 3 (S7), and the processing is completed.

In the present embodiment, the region identification section 13 identifies the whole region representing a blood vessel from a three-dimensional image, the opacity curve setting section 14 sets a base opacity curve to the identified whole region, and obtains, with respect to each of at least some of the pixels in the whole region, a representative value of pixel values in an adjacent region of a pixel concerned and sets an opacity curve obtained by changing the base opacity curve using the obtained representative value as the opacity curve to be applied to the pixel concerned in volume rendering, the image generation section 12 generates a pseudo three-dimensional image by performing volume rendering using the opacity curves set by the opacity curve setting section 14. This allows an opacity curve appropriate for depicting the pixel to be applied to each of all pixels in the region representing the blood vessel, whereby an image more accurately depicting three-dimensional morphology of the blood vessel may be generated.

Figure 3:
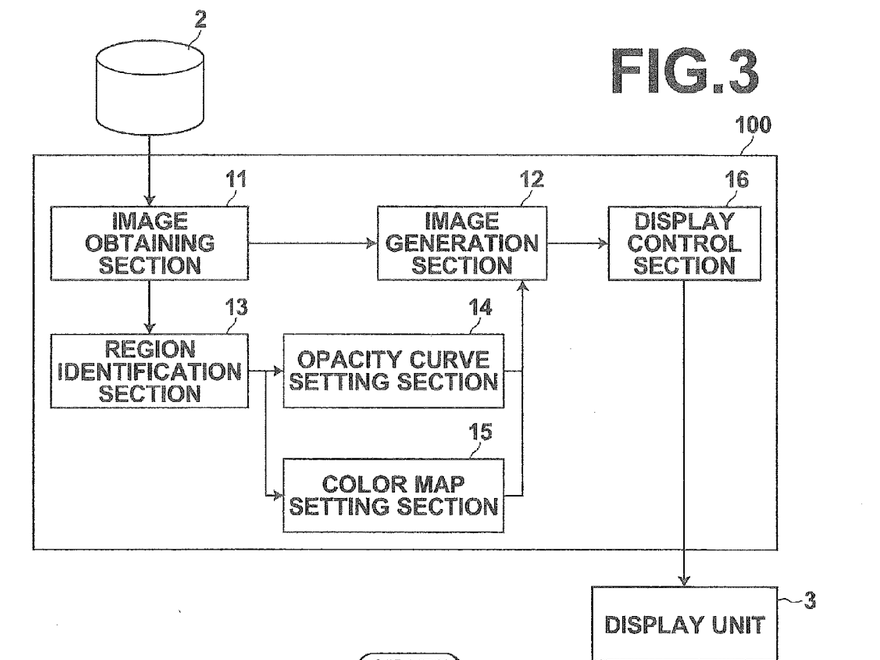
FIG. 3 is a schematic block diagram of an image generation apparatus of a second embodiment.

Next, a second embodiment of the present invention will be described. FIG. 3 illustrates an image generation apparatus according to the second embodiment of the present invention. The image generation apparatus 100 of the present embodiment includes a color map setting section 15 in addition to the configuration of the image generation apparatus 1 according to the first embodiment illustrated in FIG. 1. Other aspects are identical to those of the first embodiment.

The color map setting section 15 sets a color map to be applied to each pixel in the blood vessel region identified by the region identification section 13 in volume rendering. The color map defines the relationship between the pixel value and display color and may be represented by a function of pixel value. More specifically, a base color map is first set to the blood vessel region. Then, the color map setting section 15 obtains, with respect to each of some pixels obtained by three-dimensionally sampling the pixels in the blood vessel region at a predetermined interval, a subtraction value obtained by subtracting the average value of the pixel values in the blood vessel region from the average value of the pixel values of an adjacent region (e.g., region in the range of 1 cm in up, down, left, right, front, and back directions) of a pixel concerned as a shift amount of the color map, and sets a color map obtained by shifting the base color map by the determined shift amount in a pixel value direction to the pixel concerned as the color map to be applied to the pixel concerned. That is, the color map setting section 15 sets a color map represented, when the pixel value is taken as a variable v, the base color map is taken as ClrMapD (v), and determined shift amount is taken as m, by ClrMap (v)=ClrMapD (v−m) to each of the sampled pixels.

Further, the color map setting section 15 obtains, with respect to each of pixels other than the sampled some pixels in the blood vessel region, an estimated value of the shift amount at a pixel concerned by interpolation using the shift amount of each of the two or more sampled pixels located adjacent to the pixel concerned, and sets color map obtained by shifting the base color map by the determined estimated value in a pixel value direction as the color map to be applied to the pixel concerned.

At this time, if the shift amount and the estimated value have already obtained by the opacity curve setting section 14, the color map setting section 15 set a color map to be applied to each pixel in the blood vessel region using the shift amount and the estimated value obtained by the opacity curve setting section 14 without calculating these values. It should, of course, be appreciated that an arrangement may be made in which the opacity curve setting section 14 sets the opacity curve to be applied to each pixel in the blood vessel region using the shift amount and the estimated value obtained by the color map setting section 15.

Figure 5:
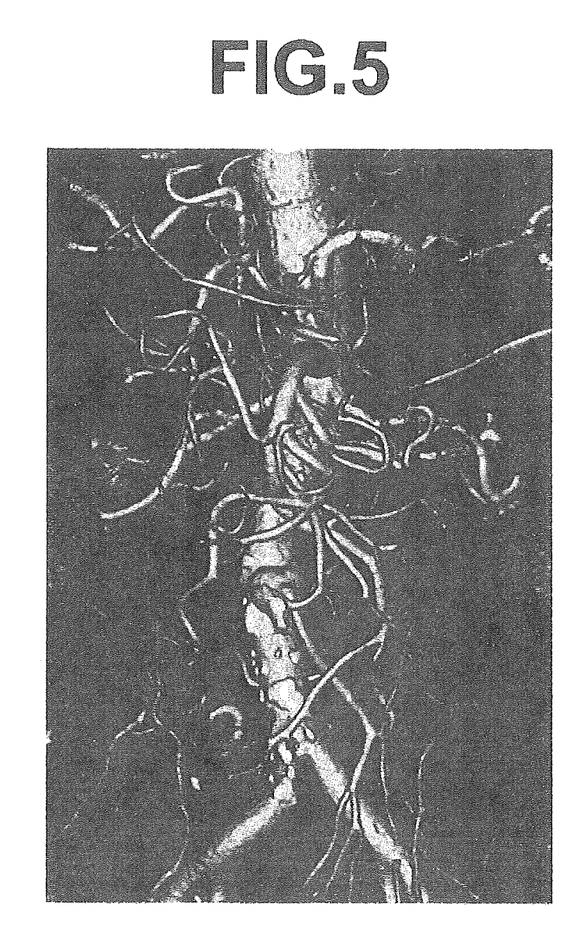
FIG. 5 is a drawing illustrating an example image generated by the image generation apparatus of the second embodiment.

The image generation section 12 generates a pseudo three-dimensional image by performing volume rendering on the three-dimensional image using the opacity curve set by the opacity curve setting section 14 and the color map set by the color map setting section 15. FIG. 5 shows an example pseudo three-dimensional image generated by the image generation apparatus 100 of the present embodiment. In FIG. 5, the three-dimensional morphology of the entire blood vessel is depicted more accurately in comparison with the images generated by performing volume rendering on the same three-dimensional image according to conventional technology shown in FIGS. 6 and 7.

Figure 4:
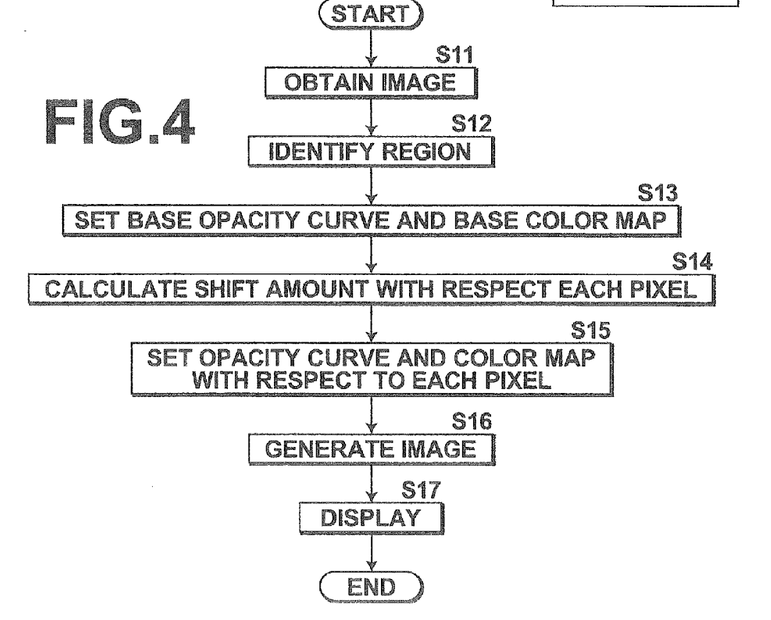
FIG. 4 is a flowchart illustrating an operation of the image generation apparatus of the second embodiment.

FIG. 4 is a flowchart illustrating an operation of the image generation apparatus 100. As illustrated, first, the image obtaining section 11 obtains a three-dimensional image stored in the storage unit 2 (S11). Then, the region identification section 13 extracts a region representing a blood vessel from the three-dimensional image obtained by the image obtaining section 11 and identifies the extracted region as a whole region (S12). Then, the opacity curve setting section 14 sets a base opacity curve to the blood vessel region and the color map setting section 15 sets a base color map to the blood vessel region (S13).

Further, the opacity curve setting section 14 or the color map setting section 15 obtains, with respect to each of some pixels obtained by three-dimensionally sampling the pixels in the blood vessel region at a predetermined interval, a subtraction value obtained by subtracting the average value of the pixel values in the blood vessel region from the average value of the pixel values of the adjacent region of a pixel concerned as a shift amount and obtains, with respect to each of pixels other than the sampled some pixels, an estimated value of the shift amount at a pixel concerned by interpolation using the shift amount of each of the two or more sampled pixels located adjacent to the pixel concerned (S14).

Then, the opacity curve setting section 14 sets, with respect to each of the sampled some pixels, an opacity curve obtained by shifting the base opacity curve by the shift amount determined in step S14 in a pixel value direction as the opacity curve to be applied to the pixel concerned and sets, with respect to each of pixels other than the sampled some pixels, an opacity curve obtained by shifting the base opacity curve by the estimated value determined in step S14 in a pixel value direction as the opacity curve to be applied to the pixel concerned. Further, the color map setting section 15 sets, with respect to each of the sampled some pixels, a color map obtained by shifting the base color map by the shift amount determined in step S14 in a pixel value direction as the color map to be applied to the pixel concerned and sets, with respect to each of pixels other than the sampled some pixels, a color map obtained by shifting the base color map by the estimated value determined in step S14 in a pixel value direction as the color map to be applied to the pixel concerned (S15).

Thereafter, the image generation section 12 generate a pseudo three-dimensional image by performing volume rendering on the three-dimensional image using the opacity curves set by the opacity curve setting section 14 and the color maps set by the color map setting section 15 (S16). Then, the display control section 16 displays the pseudo three-dimensional image generated by the image generation section 12 on the display unit 3 (S17), and the processing is completed.

In the present embodiment, the region identification section 13 identifies the whole region representing a blood vessel from a three-dimensional image, the opacity curve setting section 14 sets a base opacity curve to the identified whole region, and obtains, with respect to each of at least some of the pixels in the whole region, a representative value of pixel values in an adjacent region of a pixel concerned and sets an opacity curve obtained by changing the base opacity curve using the obtained representative value as the opacity curve to be applied to the pixel concerned in volume rendering, the color map setting section 15 sets a base color map to the identified whole region, obtains, with respect to each of at least some of the pixels in the whole region, a representative value of pixel values in an adjacent region of a pixel concerned, and sets an color map obtained by changing the base color map using the obtained representative value as the color map to be applied to the pixel concerned in volume rendering, the image generation section 12 generates a pseudo three-dimensional image by performing volume rendering using these opacity curve and color map. This allows an opacity curve and a color map appropriate for depicting the pixel to be applied to each of all pixels in the region representing the blood vessel, whereby an image depicting the three-dimensional morphology of the blood vessel more accurately may be generated.

In the present embodiment, the description has been made of a case in which both the opacity curve and the color map to be applied to each pixel in the blood vessel region are obtained by modifying the base opacity curve and the base color map respectively but an arrangement may be adopted in which, for example, the base opacity curve is used directly as the opacity curve to be applied to each pixel and only the color map to be applied to each pixel is obtained by modifying the base color map.

Further, in the embodiment described above, the description has been made of a case in which the shift amount is calculated for only some of the pixels in the blood vessel region three-dimensionally sampled at a predetermined interval and the estimated value of the shift amount is obtained by interpolation for each of the other pixels, but an arrangement may be adopted in which, with respect to each of all pixels in the blood vessel region, a shift amount is obtained based on a subtraction value obtained by subtracting a representative value of the pixel values in the blood vessel region from a representative value of the pixel values in an adjacent region of a pixel concerned and the opacity curve and/or the color map to be applied to the pixel concerned is set using the determined shift amount.

Still further, in the embodiment described above, the description has been made of a case in which the shift amount or the estimated value is obtained with respect to each pixel, but an arrangement may be adopted in which a shift amount or an estimated value is obtained with respect to each partial region constituted by two or more pixels and the opacity curve and/or the color map obtained based on the obtained shift amount or the estimated value is applied to all pixels in the partial region. That is, the opacity curve setting section 14 may be a section that obtains, with respect to each of partial regions having a predetermined size and constituting the whole region identified by the region identification section 13, a representative value of pixel values in partial region concerned and sets an opacity curve obtained by modifying the base opacity curve using the obtained representative value as the opacity curve to be applied to the partial region concerned in volume rendering, or a section that obtains, with respect to each of partial regions having a predetermined size and constituting the whole region identified by the region identification section 13, a representative value of pixel values in an adjacent region that includes a partial region concerned and sets an opacity curve obtained by modifying the set base opacity curve using the obtained representative value as the opacity curve to be applied to the partial region concerned in the volume rendering.

Likewise, the color map setting section 15 may be a section that obtains, with respect to each of partial regions having a predetermined size and constituting the whole region identified by the region identification section 13, a representative value of pixel values in partial region concerned and sets a color map obtained by modifying the base color map using the obtained representative value as the color map to be applied to the partial region concerned in volume rendering, or a section that obtains, with respect to each of partial regions having a predetermined size and constituting the whole region identified by the region identification section 13, a representative value of pixel values in an adjacent region that includes a partial region concerned and sets color map obtained by modifying the set base color map using the obtained representative value as the color map to be applied to the partial region concerned in the volume rendering.

Further, in each of the aforementioned embodiments, the description has been made of a case in which the predetermined target object is a blood vessel, but the predetermined target object may be a structure having tubular structure, such as an intestine, a bronchus, and the like, or various organs, such as a heart, a liver, and the like.

Still further, in each of the aforementioned embodiments, the description has been made of a case in which each of the representative value of pixels in the adjacent region and the representative value of pixels in the whole region is an average value, but each of the representative value of pixels in the adjacent region and the representative value of pixels in the whole region may be a mode or median value of the pixels in each region, an average value of pixels of all the pixels in each region which fall in a range of predetermined width of pixel values from the mode or median value of each region, or a mode or median value of pixels of all the pixels in each region which fall in a range of predetermined width of pixel values from the mode or median value of each region. At this time, the representative value of the pixels in the whole region may be a value of the same type as that of the representative value of the pixels in the adjacent region or a value of different type from that of the representative value of the pixels in the adjacent region.

Further, in a case where only a predetermined target object of the entire three-dimensional image is to be the visualization target region when generating an image by the volume rendering, if the region representing the predetermined target object identified by the region identification section 13 is dilated by one voxel or so and the volume rendering is performed on the dilated region, the surface of the predetermined target object may also be depicted by the volume rendering.

What is claimed is:

1. An image generation apparatus, comprising:
   a region identification section configured to identify a whole region representing a predetermined target object from a three-dimensional image;
   an opacity curve setting section configured to:
   set a base opacity curve to the identified whole region as an opacity curve that defines a relationship between a pixel value and an opacity;
   obtain, with respect to each pixel obtained by sampling pixels in the identified whole region at a predetermined interval, a representative value of pixel values in an adjacent region of a pixel concerned; and
   modify the set opacity curve using the obtained representative value; and
   an image generation section configured to generate a pseudo three-dimensional image by performing a volume rendering on the three-dimensional image, the modified opacity curve being applied to the pixel corresponding thereto in the volume rendering.

2. The image generation apparatus as claimed in claim 1, wherein the opacity curve setting section obtains, with respect to each of at least some pixels, a shift amount of the opacity curve, based on a subtraction value obtained by subtracting a representative value of pixel values in the whole region from the representative value of pixels in the adjacent region of the pixel concerned, and sets an opacity curve obtained by shifting the base opacity curve by the obtained shift amount in a pixel value direction as the opacity curve to be set to the pixel concerned in the volume rendering.

3. The image generation apparatus as claimed in claim 1, wherein the opacity curve setting section further:

obtains, with respect to each pixel of at least some pixels obtained by sampling the pixels in the whole region at a predetermined interval, a representative value of pixels in an adjacent region of a pixel concerned, obtains a shift amount of opacity curve based on a difference between the obtained representative value and a representative value of pixel values in the whole region, and sets an opacity curve obtained by shifting the base opacity curve by the obtained shift amount to a pixel value direction as the opacity curve to be applied to the pixel concerned; and obtains, with respect to each pixel of pixels in the whole region other than the sampled at least some pixels, an estimated value of shift amount at a pixel concerned by an interpolation using a shift amount of each of two or more sampled pixels located adjacent to the pixel concerned and sets an opacity curve obtained by shifting the base opacity curve by the determined estimated value in a pixel value direction as the opacity curve to be applied to the pixel concerned in the volume rendering.

4. The image generation apparatus as claimed in claim 1, wherein the representative value of the pixel values in the adjacent region comprises a mode value, a median value, or an average value of the pixel values in the adjacent region.

5. The image generation apparatus as claimed in claim 1, wherein the representative value of the pixel values in the adjacent region comprises an average value of pixel values of a portion of the pixels of all pixels in the adjacent region, wherein the portion of pixels comprises pixels which have pixel values falling in a range of a predetermined width of pixel values from a mode value or a median value of pixel values of all pixels in the adjacent region.

6. The image generation apparatus as claimed claim 1, wherein the representative value of the pixel values in the adjacent region comprises a mode value or a median value of pixel values of a portion of pixels of all pixels in the adjacent region, wherein the portion of pixels comprise pixels which have pixel values falling in a range of a predetermined width of pixel values from a mode value or a median value of pixel values of all pixels in the adjacent region.

7. The image generation apparatus as claimed in claim 1, further comprising a color map setting section configured to:

set a base color map as a color map that defines a relationship between a pixel value and a display color to the identified whole region;

calculate, with respect to each of pixels obtained by sampling the pixels in the identified whole region at a predetermined interval, a representative value of pixel values in an adjacent region of each pixel concerned; and modify the set color map using the calculated representative value, wherein the image generation section generates the pseudo three-dimensional image by performing the volume rendering on the three-dimensional image, the modified color map being applied to the pixel corresponding thereto in the volume rendering.

8. The image generation apparatus as claimed in claim 1, wherein the predetermined target object comprises a blood vessel.

9. The image generation apparatus as claimed in claim 1, wherein the opacity curve setting section is further configured to:

obtain, with respect to each of a plurality of partial regions having a predetermined size and comprising the whole region identified by the region identification section, a representative value of pixel values in a partial region concerned; and modify the set opacity curve using the obtained representative value as the opacity curve to be applied to the partial region concerned in the volume rendering.

10. The image generation apparatus as claimed in claim 7, wherein the set color map depicts a pixel for each position in the image.

11. An image generation method, the method comprising:

identifying, as executed by a processor on a computer, a whole region representing a predetermined target object from a three-dimensional image;

setting a base opacity curve to the identified whole region as an opacity curve that defines a relationship between a pixel value and an opacity;

obtaining, with respect to each pixel obtained by sampling a pixel in the identified whole region at a predetermined interval, a representative value of pixel values in an adjacent region of a pixel concerned;

modifying the set opacity curve using the obtained representative value; and generating a pseudo three-dimensional image by performing a volume rendering on the three-dimensional image, the modified opacity curve being applied to the pixel corresponding thereto in the volume rendering.

12. A non-transitory computer readable medium on which is recorded an image generation program that causes a computer to function as:

a region identification section configured to identify a whole region representing a predetermined target object from a three-dimensional image;

an opacity curve setting section configured to:

set a base opacity curve to the identified whole region as an opacity curve that defines a relationship between a pixel value and an opacity;

obtain, with respect to each pixel obtained by sampling pixels in the identified whole region at a predetermined interval, a representative value of pixel values in an adjacent region of a pixel concerned; and modify the set opacity curve using the obtained representative value; and an image generation section configured to generate a pseudo three-dimensional image by performing a volume rendering on the three-dimensional image, the modified opacity curve being applied to the pixel corresponding thereto in the volume rendering.

* * * * *